(12) United States Patent
Butler et al.

(10) Patent No.: US 7,589,539 B2
(45) Date of Patent: Sep. 15, 2009

(54) PROCESS FOR SIMULATING THE CORROSIVE EFFECTS OF REFINERY FEEDSTOCKS ON REFINERY METALURGY

(75) Inventors: Graham Butler, Churt (GB); John William Couves, Bourne End (GB); Paul Greenough, Beaconsfield (GB); Nicholas John Gudde, Windlesham (GB); Michael Graham Hodges, Wonersh (GB)

(73) Assignee: BP Oil International Limited, Middlesex (GB)

( * ) Notice: Subject to any disclaimer, the term of this patent is extended or adjusted under 35 U.S.C. 154(b) by 170 days.

(21) Appl. No.: 11/662,895

(22) PCT Filed: Sep. 14, 2005

(86) PCT No.: PCT/GB2005/003574

§ 371 (c)(1),
(2), (4) Date: Mar. 15, 2007

(87) PCT Pub. No.: WO2006/030226

PCT Pub. Date: Mar. 23, 2006

(65) Prior Publication Data

US 2008/0116907 A1    May 22, 2008

(30) Foreign Application Priority Data

Sep. 15, 2004   (GB)   ................... 0420563.9

(51) Int. Cl.
*G01R 27/08*   (2006.01)

(52) U.S. Cl. .......................... 324/700; 73/865.6; 73/86

(58) Field of Classification Search ................. 324/700, 324/71.2; 73/865.6, 86
See application file for complete search history.

(56) References Cited

U.S. PATENT DOCUMENTS

| | | | |
|---|---|---|---|
| 3,936,737 A | | 2/1976 | Jefferies, Sr. |
| 5,045,775 A | * | 9/1991 | White et al. ............... 324/71.2 |
| 5,332,900 A | | 7/1994 | Witzke et al. |
| 5,503,006 A | | 4/1996 | Babaian-Kibala et al. |
| 6,053,032 A | | 4/2000 | Kraus et al. |
| 6,683,463 B2 | | 1/2004 | Yang et al. |
| 2006/0037414 A1 | * | 2/2006 | Blum et al. ................ 73/865.6 |

FOREIGN PATENT DOCUMENTS

| | | |
|---|---|---|
| RU | 2235309 | 8/2004 |
| RU | 2240535 | 11/2004 |
| WO | WO03/069322 A2 | 8/2003 |

OTHER PUBLICATIONS

*Science*, vol. 283, Jan. 8, 1999, p. 165.

* cited by examiner

*Primary Examiner*—Vincent Q Nguyen
(74) *Attorney, Agent, or Firm*—Nixon & Vanderhye

(57) ABSTRACT

Process for evaluating the corrosive effect of a refinery feedstock on the metallurgy of one or more refinery processes, by (i) providing a plurality of refinery feedstocks and/or a plurality of fractions of one or more refinery feedstocks, (ii) providing an array having a plurality of metal samples representative of metallurgy present in a refinery, (iii) contacting each of the plurality of metal samples with one or more of the refinery feedstocks or fractions under non-static conditions, and (iv) determining the corrosive effect of the feedstock and/or fraction on the metal sample.

12 Claims, 2 Drawing Sheets

PROCESS FOR SIMULATING THE CORROSIVE EFFECTS OF REFINERY FEEDSTOCKS ON REFINERY METALURGY

This application is the U.S. National Phase of International Application PCT/GB2005/003574, filed 14 Sep. 2005, which designated the U.S. PCT/GB2005/003574 claims priority to British Application No. 0420563.9 filed 15 Sep. 2004. The entire content of these applications are incorporated herein by reference.

BACKGROUND OF THE INVENTION

This invention relates to processes for the evaluation of the effect of refinery feedstocks on refinery processes using high throughput experimentation.

Corrosion is a major operational issue in oil refineries, with implications for availability and safety, and in some cases, limiting the amount of crude oil that can be processed. Refinery corrosion can be caused by the crude itself or by particular fractions thereof, and is highly feedstock dependant and blend dependant. Existing methods of evaluating the corrosive effect of feedstocks are slow and not always reliable. The present invention allows high blends to be explored more effectively than known methods, and compared with known methods, provides more information in a more timely fashion.

SUMMARY OF THE INVENTION

Results obtained from the process enable decisions on how to process a particular crude to be made, because the blend structure can be explored before processing, whereas existing methods require inference from previous knowledge.

Combinatorial or high throughput chemistry has revolutionized the process of drug discovery. See, for example, 29 Acc. Chem. Res. 1-170 (1996); 97 Chem. Rev. 349-509 (1997); S. Borman, Chem. Eng. News 43-62 (Feb. 24, 1997); A. M. Thayer, Chem. Eng. News 57-64 (Feb. 12, 1996); N. Terret, 1 Drug Discovery Today 402 (1996)). Over recent years, a number of high throughput experimentation techniques have been developed to allow significant increases in the ability to synthesize and test catalytic and other materials for useful properties. In general, such techniques have focussed on development of apparatus and methodologies, including the growing use of robots and computers to design experiments and to automate catalyst and materials preparation and testing, to allow rapid and reproducible testing results to be achieved on relatively small scale samples. For example, much effort has gone in to developing preparation and testing apparatus for numerous types of materials and material properties (such as described in U.S. Pat. No. 5,776, 359) and for chemical reactions of interest (such as described in U.S. Pat. Nos. 5,959,297, 6,063,633 and 6,306,658).

In addition, high throughput techniques have been applied to many different analytical techniques, including separation techniques such as chromatography (such as described in U.S. Pat. No. 6,866,786). Also, cost of components has been used as a factor in the design of libraries or arrays (such as described in U.S. Pat. No. 6,421,612).

The high throughput technologies have generally focussed on discovery of new catalysts and materials for existing processes, but Barbour et al, SCIENCE, 283, 8 Jan. 1999 describes a technique for testing corrosion by creating a grid of differing conditions in a thin copper film. The thickness of a copper oxide coating on a plate was increased in one dimension, while the number of defects was increased in the other dimension. The foil was then exposed with air spiked with hydrogen sulphide to study the resulting corrosion. Such a system, however, only provides limited information, and is not able to predict accurately the effects of dynamic flow conditions such as those experienced in a refinery. We have now developed high throughput methodologies that can be applied to evaluating the corrosive effect of a refinery feedstock on the metallurgy of a refinery process.

Thus, according to the present invention there is provided a process for evaluating the corrosive effect of a refinery feedstock on the metallurgy of one or more refinery processes, said process comprising:

(i) providing a plurality of refinery feedstocks and/or a plurality of fractions of one or more refinery feedstocks, (ii) providing an array comprising a plurality of metal samples representative of metallurgy present in a refinery, (iii) contacting each of the plurality of metal samples with one or more of said refinery feedstocks or fractions under non-static conditions, and (iv) determining the corrosive effect of said feedstock and/or fraction on the metal sample.

Any suitable refinery feedstock may be used, including a crude oil, a synthetic crude, a biocomponent, an intermediate stream, such as a residue, gas oil, vacuum gas oil, naphtha or cracked stock, and blends of one or more of said components, such as a blend of one or more crude oils or a blend of one or more crude oils with one or more synthetic crudes.

On a typical refinery, a number of different refinery feedstocks are processed, such as a number of different crude oils. The refinery feedstocks are also usually blends of available feeds, and thus, it is very difficult to predict the effect of the feedstock on the overall refinery process. Because existing methods are slow and expensive, it is not feasibly to explore the corrosivity of all fractions of all blends. Typically, a number of assumptions are made on the basis of previous operating experience, but these can usually only provide a qualitative prediction.

The present invention provides a process for the evaluation of the effect of a refinery feedstock on the metallurgy of one or more refinery processes that allows the potential process issues of using a refinery feedstock to be evaluated prior to its use, and potentially even before its purchase. The present invention can also aid selection of the most appropriate refinery at which a feedstock should be processed where more than one option is available. Unlike previous methods of testing, the present invention, using high throughput techniques, permits testing to be carried out using a multiplicity of feedstocks and/or fractions, typically all relevant feedstocks and/or fractions, each of which can be tested against a selected metal sample. In effect, an array of feedstocks and/or fractions can be tested against an array of metal samples, to provide a large quantity of data which can be manipulated to provide corrosion "maps". The throughput of the overall workflow is important, with the rate of provision of refinery feedstocks and/or fractions in step (a) preferably being at least 50 per week, for example at least 250 per week, especially at least 2000 per week, and the rate of determination of the corrosive effect of step (d) preferably being at least 250 per week, for example at least 1250 per week, especially at least 10,000 per week.

"Corrosive effects" that may be evaluated by the process of the present invention include corrosion caused by sulphidic species such as hydrogen sulphide, mercaptans and organic sulphides (generally termed "reactive sulphur compounds"), corrosion caused by organic carboxylic acids, such as alkyl chain carboxylic acids, cycloalkyl (1-5 rings) carboxylic acids, aromatic carboxylic acids (generally termed "naphthenic acids") and corrosion caused by inorganic acids e.g. hydrogen chlorides (generally called "mineral acids").

At any time, the above three corrosion mechanisms in refinery feedstocks (sulphidic, naphthenic, mineral acid) based on the presence and types of sulphidic (reactive) sulphur, naphthenic acid, and mineral acids, are in competition. These mechanisms may work synergistically to and give reduced corrosion compared to the effect of each component or antagonistically to give enhanced corrosion. For example sulphidic (reactive) sulphur when present at low to medium levels forms a passivation layer (Iron sulphide, FeS) on metal surface which reduces the rate of naphthenic acid corrosion. Thus refiners often process naphthenic acid crudes with high sulphur crudes to reduce corrosion risk and increase the portion of lower cost acid crude which can be processed. However at high sulphidic sulphur levels then the sulphidic sulphur enhances the rate of naphthenic acid corrosion. Further this relationship is complicated by flow rate and temperature. Thus conventional models are unable to predict this. Current methods of corrosion determination, measured in weeks per test, do not permit the generation of a matrix of conditions necessary to map out the corrosion relationship based on velocity, temperature, sulphidic sulphur and naphthenic acid. Thus refiners must be conservative and process lower levels of acid crude. The use of high throughput techniques enables refiners to measure blends under a wide range of conditions to truly map the corrosion rate surface and access the synergistic benefits and enhance low cost crude processing, adding to refinery margin.

The plurality of metal samples representative of metallurgy present in a refinery suitably represent the metallurgy that may be present at refinery processes in the refinery prone or potentially prone to corrosion. Typical metallurgies include Carbon Steel (CS), Chromium steels (such as 5Cr, 9Cr), Stainless steels (such as 410, 316 (with less than 2.5% Mo), 317, 321, 825)).

Typically, refinery processes in the refinery prone or potentially prone to corrosion are processes where heating of the refinery feedstock occurs, where fluids travel at high velocity or sheer and/or where high concentrations of corrosive materials may be present, such as in the crude distillation column (CDU), reboiler, heat-exchanger and furnace tubes, the vacuum column, overhead condensation systems, transfer lines, heaters for coking units, hydrotreating process and hydrocracking process.

Typically, the plurality of metal samples will comprise at least 5 metal samples, for example at least 10 metal samples, such as at least 20 metal samples.

The process of the present invention may be performed using a microfabricated array of metal samples.

The metal samples may be representative of metallurgies present in a particular individual refinery or of a number of differing metallurgies present in two or more refineries.

Metal samples representative of other metallurgies may also be present, but typically the majority of the metals present will be representative of metallurgies already present in one or more refineries.

In one embodiment, the plurality of metal samples may be a plurality of different metal samples chosen to cover a spectrum of metal samples present in a refinery, such that a number of metal samples may be evaluated in parallel. Alternatively, the plurality of metal samples may all be one type of metal sample or only a few different metal samples, such as only 2 to 3 different metal samples, and the process of the present invention may be (predominantly) used to evaluate the effects of differences in process conditions and/or in the properties of the fractions representative of the typical feedstock, as described further below.

In step (iii) of the present invention each of the plurality of metal samples is contacted with the refinery feedstock or a fraction thereof. Preferably each contact made is made in parallel, i.e. each contact is made simultaneously.

The refinery feedstock or fraction thereof should be representative of the refinery stream that would typically be in contact with the respective metallurgy in a refinery process. By "representative of" is meant having at least some similar chemical and/or physical properties as the typical refinery stream to the refinery process. For example, the plurality of fractions may have a boiling point range typical for the feedstock to the equivalent process on a refinery. A fraction with the desired boiling point range may be obtained by use of a suitable separation means, such as distillation.

Chemical and physical properties of the feedstock to a particular refinery process will depend on a particular refinery configuration, but typical properties are described, for example, in Handbook of Petroleum Refining Processes ($2^{nd}$ Edition), edited by Robert A Meyers and published by McGraw-Hill.

For example, in a refinery the metallurgy in the heating section of a crude distillation column typically is exposed to the entire refinery feedstock. Hence, in the present invention, samples representative of these metallurgies are contacted with a sample of the fall refinery feedstock. In contrast, the metallurgy in specific regions of a crude distillation unit (CDU) or vacuum distillation unit (VDU) and in the pipework associated with specific fractions in the distillation tower and pipework connecting to down stream process units, or in heating before certain process units typically is only exposed to fractions of said refinery feedstock, and hence, in the present invention, the refinery feedstock is treated to produce a representative fraction which is contacted with the representative metal sample(s).

Any suitable physical or chemical treatment method may be used to obtain the fractions representative of the typical feedstock for said refinery process. For example, a microdistillation column or microfractionator may be used on each portion to obtain fractions with defined boiling point ranges. Other techniques may include solvent extraction, membrane treatments, adsorption treatments and suitable chemical reactions. Combinations of techniques may be required, for example, micro-distillation followed by a chemical reaction to represent crude oil distillation followed by a conventional treatment of said fraction that occurs before the process of interest in a refinery. For example, the feedstock to catalytic reforming process is typically hydrotreated before said reforming process.

The representative fraction will typically be a fraction within a limited boiling point range.

Thus, in a preferred embodiment, the refinery feedstock is divided to produce a plurality of portions, one for each of the plurality of metal samples, wherein each portion is treated, where necessary, to produce a fraction with a boiling point range within the range required for contact with the metal sample.

The dividing may be achieved by any suitable means. For example, the dividing may be performed in a batch mode by using one or more automated syringes to provide the plurality of portions. Alternatively, a series of microflow controllers or microvalves may be used in which the flow for each portion is generally continuous, but can be started and stopped, and optionally varied, using the valve or controller. As a further alternative, a plurality of baffles or other flow control means, such as orifices in a plate, where flow can't be shut-off or varied independently for each portion, but which provide an even flow distribution across the plurality of portions, may be used.

In one embodiment, the portion is placed on a heating device, heat is then applied to increase the sample temperature, and the fraction which boils between the desired ranges is collected, for example, by using a suitable valve to collect the fraction of the correct boiling range, which is then cooled to condense said fraction. The heating device may be a heated microoscillator, as described in U.S. Pat. No. 5,661,233.

In another embodiment, each portion may be placed in an enclosed channel comprising at least three sections, each section separated by valves or other suitable barriers which liquid samples cannot pass, but gaseous samples can. Thus, each portion may be placed in the first section of a channel and the first section heated to the upper boiling point of the boiling point range desired, for example using a heating laser to give local heating, and the second section may be maintained at ambient temperature (or below), such that all material with a boiling point below the upper boiling point vaporises and passes from the first section into the second section, where it condenses.

The second section is then heated to the lower boiling point of the range desired, for example using a heating laser to give local heating, and the third section is maintained at ambient temperature (or below), wherein all material with a boiling point below the lower boiling point vaporises and passes from the second section into the third section, leaving, in the second section, a fraction with the desired boiling point range.

Alternatively, the second section may maintained at the lower boiling point throughout, such that material with a boiling point above the range desired remains in section 1, material with a boiling point in the range desired is collected in section 2, and material with a boiling point below the range desired is collected in section 3.

A plurality of channels, each having the at least three sections may be provided on a spinning disk-type separation device as described in WO 01/87485 or WO 2004/58406. In a further embodiment, further sections comprising one of the plurality of metal samples may also be provided for each channel on a spinning disc, and the contacting of the metal sample with the refinery feedstock or a fraction thereof may also be performed on the spinning disc.

The contacting of each of the plurality of metal samples with the refinery feedstock or a fraction thereof should be under non-static conditions, i.e. varying conditions, typically representative of those to which the equivalent metallurgy would be exposed in the refinery. Conditions which may be varied include temperatures, flow rates, sheer, soak, condensation and/or turbulence. In one embodiment, these conditions will be equivalent to those in the refinery, such as the same temperatures and/or flow rates. In an alternative embodiment, more severe conditions than those to which the equivalent metallurgy would be exposed in the refinery, such as higher temperatures, increased flow, sheer or turbulence, may be used to enhance corrosion rates and enable relative results for different feedstocks to be obtained more rapidly. Typically, the results present the corrosion rate as a function of flow, shear, temperature, pressure, feedstock and/or fraction.

A range of temperatures and other operating conditions, including variation in the boiling point range of the refinery feedstock fraction where appropriate, can be evaluated, optionally in parallel, giving information on the options for mitigating potential problems by process control.

Typical non-static conditions include, for example, covering the metal sample with the refinery feedstock or a fraction thereof in a suitable reaction well, under "flow" conditions, for example, by continually flowing the refinery feedstock or a fraction thereof over the metal sample, or under sheer (moving, e.g. rotating, the metal sample in the fluid) or turbulence, or under variable temperature or pressure conditions.

In step (iv) the corrosive effect of said feedstock on the metals is determined. This may be by any suitable means, such as visual analysis (for example, using a microscope, or colour monitoring for corrosion products formation) or surface analysis using a suitable analytical technique. A preferred method involves measuring the concentration of corrosion metals in solution.

In one embodiment of the present invention, the metal samples are in a form which has a non-negligible resistance, such as wires, thin sheets or meshes. Such samples have the advantage that their resistance, and any changes therein, can be readily measured. Thus, any corrosion of the metal samples will be measurable by changes in resistance of the samples. Such samples can be heated and their temperature can be accurately controlled and monitored by resistive heating. Such samples can be prepared by any known method.

Thus, one embodiment of the process of the present invention comprises flowing the refinery feedstock or fractions thereof over a plurality of resistively heated metal wire or mesh samples and measuring the resistance change with time to determine the rate of corrosion of said metal samples.

Whatever method of determining the corrosive effect of the feedstock and/or fraction is chosen, the determination for each metal sample may be carried out in parallel (i.e. each analysis is carried out simultaneously) or in series, for example using rapid serial analysis.

Using the process of the present invention, the potential for corrosion problems in various parts of a refinery process from a particular refinery feedstock can be rapidly evaluated.

Using the process of the present invention mitigation steps, such as careful process control and/or addition of corrosion inhibitors (which can be added specifically as and where needed in the refinery process) can be assessed. Thus known or new corrosion inhibiting chemicals can be added at different levels to feedstocks or fractions, the treated feedstock or fraction thereof then being contacted with a plurality of different metal samples, or being contacted with only 1 or 2 different metal samples under a range of conditions of flow and temperature, and the rate of corrosion of metal samples determined, thus determining the suitability of the additive(s) to a particular part of a refining process or particular metallurgy.

The process of the present invention may also be applied to blends of the refinery feedstock to be evaluated with other feedstocks, and hence used to evaluate the effect of the blended feedstock on the corrosion problems in various parts of a refinery process.

The process of the present invention may be repeated for a number of different potential refinery feedstocks.

The different refinery feedstocks to be evaluated may be separate (independent) feedstocks or may be blends, for example, in different ratios, of two or more other refinery feedstocks.

Alternatively, a number of different potential refinery feedstocks can be evaluated simultaneously, each, or a fraction of each, being fed to a plurality of metal samples representative of metallurgy present in a refinery as described above.

BRIEF DESCRIPTION OF THE DRAWINGS

The invention will be further described with reference to the accompanying drawings, in which.

An example of the evaluation of corrosion using a particular embodiment of the invention is given below.

EXAMPLE

A process for evaluating the corrosive effect of a refinery feedstock on the metallurgy of one or more refinery processes can be implemented in a system comprising a parallel 96 channel reciprocating shuttle corrosion reactor. The corrosion reactor includes 96 test cells arranged in eight 12-cell metal blocks. Each block includes a two-part housing in the shape of a disc, including a lower portion with indentions for each of the test cells, and provides a uniform thermal environment for all twelve cells in the unit. The test cells are set in the indentions and an upper portion of the housing is pressed against the lower portion to form a seal around each of the test-cell indentions.

Each test cell is fabricated from ceramic or ceramic coated stainless steel. The test cell is in the shape of a hollow cylinder, with an indentation for receiving a 1" long by 1/16" diameter metal corrosion coupon along the central axis of the test cell. An annular magnetic shuttle fits within the test cell cylinder and around the metal coupon, such that a defined space exists between the coupon and shuttle. Magnetic coupling is produced by a rotating quadrupole magnetic assembly located directly below the housing.

In operation, a robotic liquid sample preparation and loading system is used to dispense a known amount (approximately 450 mg) of a test liquid representing, e.g., one of a plurality of different crude distillate fractions, into each cell in the reactor. After loading, each test cell is placed into an indentation in one of the 12-cell reactor block. A metal corrosion coupon and magnetic shuttle are added to each cell. Up to eight such blocks are loaded (such that up to 96 different liquid/metal pairs can be tested) and the blocks are sealed under inert atmosphere.

Each block is heated to a predetermined temperature and the magnets associated with each block are rotated to drive the shuttle in each cell. The magnetic force causes each shuttle to be alternately repelled or attracted generating a vertical reciprocating motion within each test cell. As the magnetic shuttle is driven from one end of the test cell to the other, it displaces the liquid contained in the cell, forcing the liquid through the narrow annular space between shuttle and pin and generating an alternating high velocity flow. This motion creates a controlled cyclical wall shear-stress at the surface of the corrosion coupon simulating shear stress experienced in pipes or other commercial fluid devices. This reciprocating shuttle motion is continued at the set temperature for between 1 and 48 hours.

Figure 1:
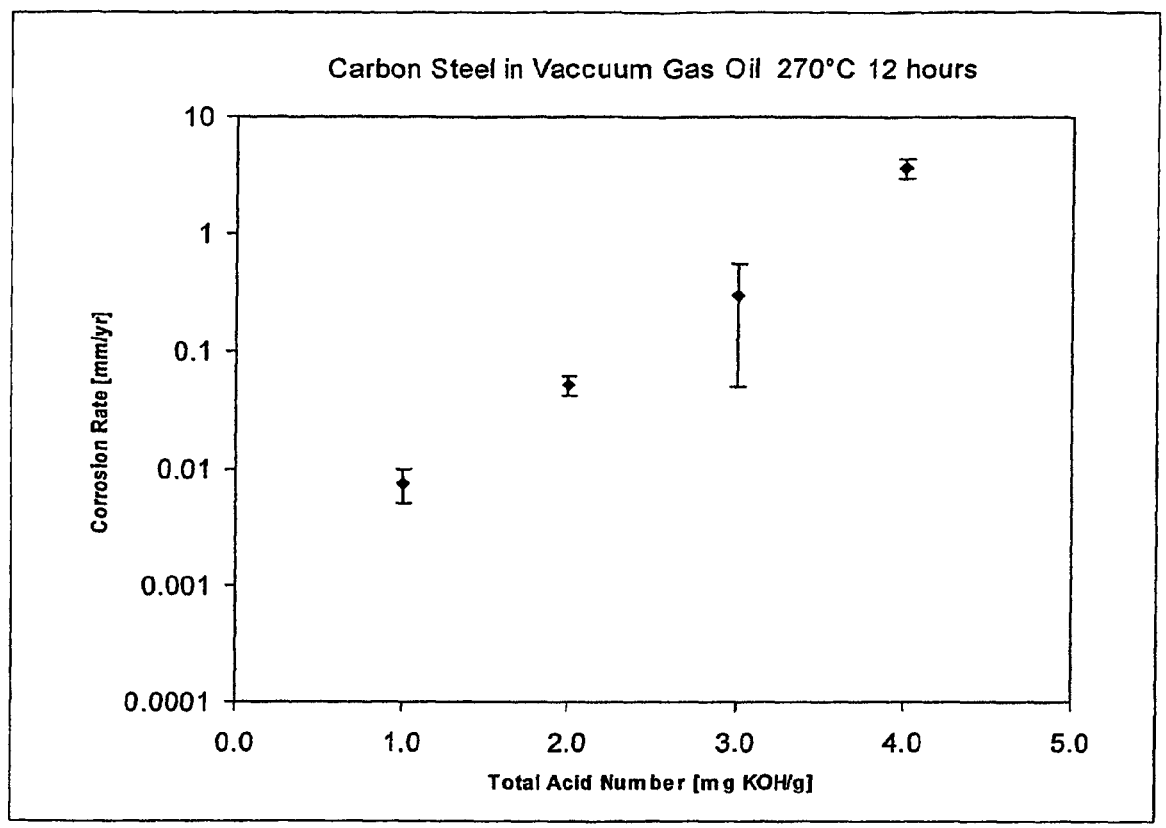
FIG. 1 which shows plot of corrosion rate versus total acid number for carbon steel in vacuum gas oil 270° C. 12 hours.
Figure 2:
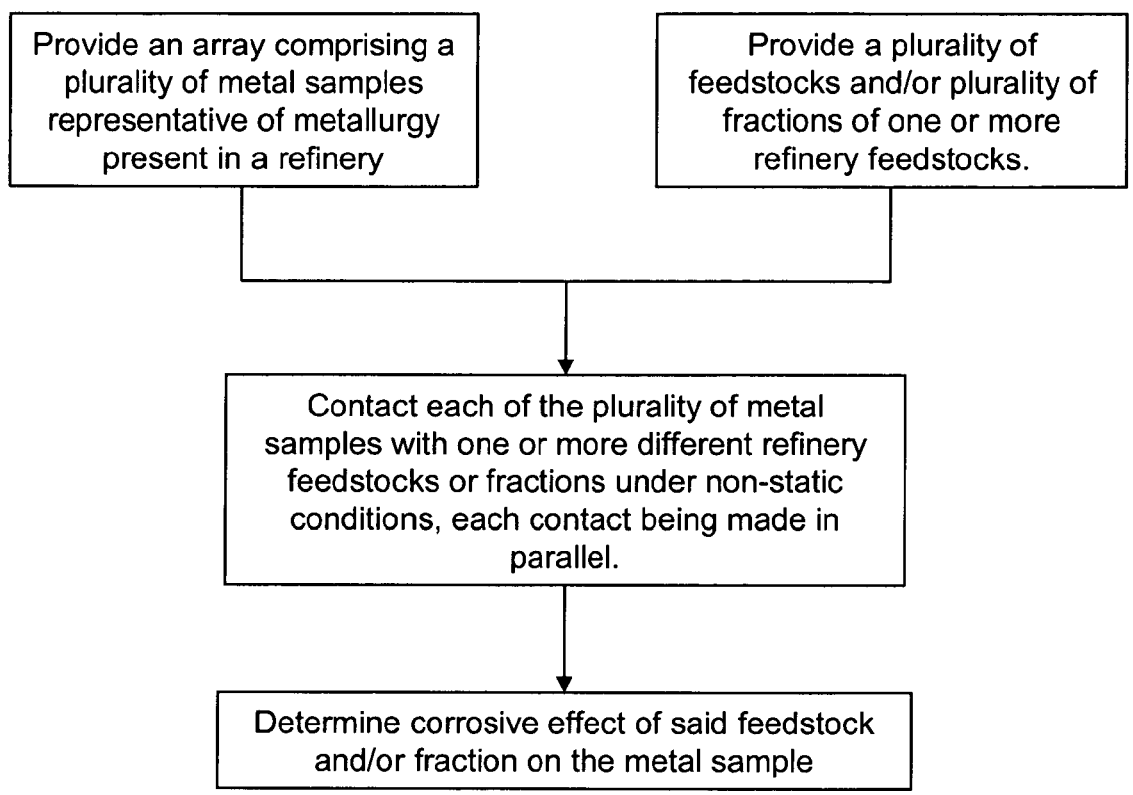
FIG. 2 is a block diagram illustrating the claimed process.

Each reactor block is then opened, and the robotic liquid sample preparation and loading system is used to transfer a sample of each test liquid (approximately 150 mg) to a glass vial and dilute the liquid by a factor of 20 (w/w) with Premi-Solv ICP solvent (Conostan/ConocoPhillips Co.). The diluted samples are then heated and mixed. The concentration of one or more elements (e.g., iron) in the diluted test liquid is then determined by inductively coupled plasma—optical emission spectrometry (ICP-OES, IRIS Intrepid II XSP with Cetac auto-sampler, Thermo Electron Corp.). A corrosion index (in mm per year) is calculated for each liquid/metal pair from the measured concentration of corrosion products, which is expected to correlate with long-term corrosion rates for the metal. Results obtained over a 12 hour period at 270° C. for a carbon steel test sample in vacuum gas oil at four different Total Acid Number values are shown in FIG. 1.

The invention claimed is:

1. A process for evaluating the corrosive effect of a refinery feedstock on the metallurgy of one or more refinery processes, said process comprising:
   (i) providing a plurality of refinery feedstocks and/or a plurality of fractions of one or more refinery feedstocks,
   (ii) providing an array comprising a plurality of metal samples representative of metallurgy present in a refinery,
   (iii) contacting each of the plurality of metal samples with one or more different refinery feedstocks or fractions under non-static conditions, and
   (iv) determining the corrosive effect of said feedstock and/or fraction on the metal sample wherein each contact of step (iii) is made in parallel.

2. A process as claimed in claim 1, in which the refinery feedstock is selected from a crude oil, a synthetic crude, a biocomponent, an intermediate stream, and blends thereof.

3. A process as claimed in claim 2, in which the refinery feedstock is selected from a residue, gas oil, vacuum gas oil, naphtha or cracked stock, and blends thereof.

4. A process as claimed in claim 1, in which the metal samples representative of metallurgy present in a refinery are selected from carbon steel, chromium steel, and stainless steel.

5. A process as claimed in claim 1, carried out using a microfabricated array of metal samples.

6. A process as claimed in claim 1, in which a plurality of fractions of one or more refinery feedstocks is obtained by using a microdistillation column or microfractionator.

7. A process as claimed in claim 1, in which a refinery feedstock is divided to produce a plurality of portions, one for each of the plurality of metal samples, wherein each portion is treated to produce a fraction with a specific boiling point range for contact with the metal sample.

8. A process as claimed in claim 1, in which the non-static conditions of step (iii) involve contacting the metal samples with the refinery feedstock and/or fraction under variable flow conditions, variable sheer conditions, and/or variable temperature conditions.

9. A process as claimed in claim 1, in which the metal samples are in the form of wires, thin sheets or meshes.

10. A process as claimed in claim 9, in which the temperature of the metal samples is controlled and monitored by resistive heating.

11. A process as claimed in claim 10, in which the refinery feedstock(s) and/or fraction(s) is caused to flow over a plurality of resistively heated metal wire or mesh samples and the resistance change with time is measured to determine the rate of corrosion of said metal samples.

12. A process as claimed in claim 1, in which the corrosive effect is measured by measuring the concentration of corrosion metals in solution.

* * * * *